US009597019B2

(12) United States Patent
Ray et al.

(10) Patent No.: US 9,597,019 B2
(45) Date of Patent: Mar. 21, 2017

(54) METHOD OF ENSURING DATE AND TIME ON A TEST METER IS ACCURATE

(75) Inventors: Pinaki Ray, Fremont, CA (US); Greg Matian, Foster City, CA (US); Carrie Arndt, Pleasanton, CA (US); Ulrich Kraft, Hofneim (DE); Eric Bailey, Oakland, CA (US); Murphy Freelen, Menlo Park, CA (US); Mark H. Olson, San Carlos, CA (US); David Taylor, Alloa (GB)

(73) Assignee: LifeScan, Inc., Wayne, PA (US)

( * ) Notice: Subject to any disclaimer, the term of this patent is extended or adjusted under 35 U.S.C. 154(b) by 2062 days.

(21) Appl. No.: 11/704,526

(22) Filed: Feb. 9, 2007

(65) Prior Publication Data
US 2008/0194934 A1   Aug. 14, 2008

(51) Int. Cl.
*A61B 5/00* (2006.01)
*A61B 5/145* (2006.01)
(Continued)

(52) U.S. Cl.
CPC ... *A61B 5/14532* (2013.01); *G01N 33/48792* (2013.01); *G06F 19/322* (2013.01); *G06F 19/3406* (2013.01); *G06F 19/3412* (2013.01); *A61B 5/1477* (2013.01); *A61B 5/14551* (2013.01); *A61B 2560/0276* (2013.01); *A61B 2562/0295* (2013.01)

(58) Field of Classification Search
USPC ...... 702/79, 89, 176–178, 19; 600/345, 347, 600/365
See application file for complete search history.

(56) References Cited

U.S. PATENT DOCUMENTS 5,042,937 A * 8/1991 Cornsweet .................. 351/204
5,740,460 A * 4/1998 Wise et al. .................. 348/473
(Continued)

FOREIGN PATENT DOCUMENTS

EP   1365523 A2   11/2003
EP   1391794 A1    2/2004
(Continued)

OTHER PUBLICATIONS

OneTouch Diabetes Management Software v.2.3.1 User Manual, 2006 LifeScan, Inc. Milpitas, CA 95035 Rev. date Jul. 2006 AW 064-350-01A, pp. 1-173.
(Continued)

*Primary Examiner* — Patricia Mallari
*Assistant Examiner* — Karen Toth (57) ABSTRACT

A method of operating a glucose test meter is provided. The method can be achieved by storing a plurality of glucose readings to a first memory of the test meter, each of the glucose readings having a time stamp and an order index, the time stamp comprising a date and a time when the glucose reading was performed, the order index indicating an order in which the plurality of glucose readings was saved to the first memory; determining whether successively saved glucose readings have time stamps in chronological order consistent with the order index; and indicating that the date and the time setting in the test meter is incorrect if there are successively saved glucose readings having time stamps inconsistent with the order index.

22 Claims, 6 Drawing Sheets

(51) Int. Cl.
  *G06F 19/00* (2011.01)
  *G01N 33/487* (2006.01)
  *A61B 5/1455* (2006.01)
  *A61B 5/1477* (2006.01)

(56) References Cited

U.S. PATENT DOCUMENTS

| | | | |
|---|---|---|---|
| 6,377,894 B1 | 4/2002 | Deweese et al. | |
| 6,516,221 B1 | 2/2003 | Hirouchi et al. | |
| 6,564,218 B1* | 5/2003 | Roth | |
| 6,600,997 B2 | 7/2003 | Deweese et al. | |
| 6,658,403 B1* | 12/2003 | Kuroda et al. | |
| 7,234,166 B2* | 6/2007 | Nurmela | 726/23 |
| 7,340,610 B1* | 3/2008 | Yagawa | 713/178 |
| 2003/0017870 A1* | 1/2003 | Klein | 463/25 |
| 2003/0152177 A1* | 8/2003 | Cahill-O'Brien et al. | 375/354 |
| 2003/0211617 A1* | 11/2003 | Jones | A61B 5/14532 436/14 |
| 2004/0057340 A1 | 3/2004 | Charles-Erickson et al. | |
| 2004/0107389 A1* | 6/2004 | Brown et al. | 714/50 |
| 2004/0133455 A1 | 7/2004 | McMahon | |
| 2005/0138383 A1* | 6/2005 | Vainstein | 713/178 |
| 2005/0149615 A1* | 7/2005 | Nedimyer et al. | 709/202 |
| 2005/0267780 A1 | 12/2005 | Ray et al. | |
| 2006/0279431 A1 | 12/2006 | Bakarania et al. | |
| 2007/0030821 A1* | 2/2007 | Iwamura et al. | 370/328 |
| 2007/0086487 A1* | 4/2007 | Yasuda et al. | 370/503 |
| 2007/0129621 A1 | 6/2007 | Kellogg et al. | |
| 2008/0027961 A1* | 1/2008 | Arlitt et al. | 707/101 |
| 2008/0043743 A1* | 2/2008 | Nagana | 370/394 |
| 2008/0194934 A1 | 8/2008 | Ray et al. | |
| 2009/0150416 A1* | 6/2009 | Baker et al. | 707/100 |
| 2010/0132085 A1* | 6/2010 | Beaudet | 2/6.5 |
| 2010/0156633 A1* | 6/2010 | Buck et al. | 340/540 |
| 2011/0015509 A1* | 1/2011 | Peyser | 600/347 |
| 2011/0178717 A1* | 7/2011 | Goodnow et al. | 702/19 |
| 2013/0266005 A1* | 10/2013 | Pegrum et al. | 370/355 |

FOREIGN PATENT DOCUMENTS

| | | |
|---|---|---|
| EP | 1727065 A1 | 11/2006 |
| GB | 2322207 A | 8/1998 |
| JP | H11281779 A | 10/1999 |
| JP | 2000-060803 | 2/2000 |
| JP | 2006-239062 | 9/2006 |
| JP | 2006-346450 | 12/2006 |
| WO | WO 01/18998 A1 | 3/2001 |
| WO | WO 01/24427 A1 | 4/2001 |
| WO | WO 2004/027676 A2 | 4/2004 |
| WO | WO 2006/133435 A2 | 12/2006 |

OTHER PUBLICATIONS

Micael A. Lombardi "Radio Controlled Clocks" National Institute of Standards and Technology (NIST) Boulder, Colorado 80305, 2003 NCSL International Workshop and Symposium, pp. 1-18.
Stevens, M.W.: "Unification of relative time frames for digital forensics" , vol. 1, No. 3, Sep. 1, 2004, pp. 225-239, XP004552533.
European Search Report, European Patent Application No. 08250484.6, dated May 14, 2009, Munich Germany,.
Japanese Application No. 2008-029667, Notice of Reasons for Rejection, Japanese Patent Office, Sep. 12, 2012, 2 pages.
Israel Registrar of Patents, Israel Patent Application No. 188783, Notification of Defects dated May 14, 2012, 2 pages.
Taiwan Application No. 97104409, Search Report, TIPO, Jun. 26, 2013, 1 page.
Search Report issued in related Chinese Patent Application No. 201110378761.7, dated Jan. 17, 2014, 2 pages.
First Office Action issued in related Chinese Patent Application No. 2011103787617, dated Jan. 28, 2014, 11 pages.
Second Office Action issued in related Chinese Patent Application No. 2011103787617, dated Mar. 27, 2015, 10 pages.
First Office Action issued in related Chinese Patent Application No. 200810074209.7, dated Jul. 14, 2010, 8 pages.
Second Office Action issued in related Chinese Patent Application No. 2008100742097, dated Jul. 14, 2010, 10 pages.
Examination Report issued in related European Patent Application No. 08250484.6, dated Jan. 7, 2010, 3 pages.
Notice of Preliminary Rejection issued in related Korean Patent Application No. 10-2008-0011822, mailed Oct. 22, 2013, 11 pages.
Notice of Final Rejection issued in related Korean Patent Application No. 10-2008-0011822, mailed Oct. 22, 2013, 6 pages.
Examination Report issued in related Mexican Patent Application No. MX/a/2008/002033, issued Jul. 15, 2011, 3 pages, with partial English translation.
Office Action issued in related Russian Patent Application No. 2008104909, issued Jan. 12, 2012, 10 pages.
Exam Report issued in related Canadian Patent Application No. 2,619,133, issued Jan. 23, 2015, 4 pages.

* cited by examiner

| Relative Order | Time Stamp Order | Time Stamp | | Glucose Concentration | Comments |
|---|---|---|---|---|---|
| | | Date | Time | | |
| 8 | 8 | 1/2/2006 | 10:00 PM | 95 | |
| 7 | 7 | 1/2/2006 | 6:00 PM | 300 | |
| 6 | 6 | 1/2/2006 | 12:00 PM | 95 | |
| 5 | 5 | 1/2/2006 | 9:00 AM | 82 | |
| 4 | 4 | 1/1/2006 | 10:00 PM | 100 | |
| 3 | 3 | 1/1/2006 | 6:00 PM | 400 | |
| 2 | 2 | 1/1/2006 | 12:00 PM | 200 | |
| 1 | 1 | 1/1/2006 | 9:00 AM | 80 | |

*FIG. 3*

| Relative Order | Time Stamp Order | Time Stamp | | Glucose Concentration | Comments |
|---|---|---|---|---|---|
| | | Date | Time | | |
| 6 | 8 | 1/2/2006 | 12:00 PM | 95 | |
| 5 | 7 | 1/2/2006 | 9:00 AM | 82 | |
| 4 | 6 | 1/1/2006 | 10:00 PM | 100 | |
| 3 | 5 | 1/1/2006 | 6:00 PM | 400 | |
| 2 | 4 | 1/1/2006 | 12:00 PM | 200 | |
| 1 | 3 | 1/1/2006 | 9:00 AM | 80 | |
| 8 | 2 | 12/31/2005 | 10:00 PM | 95 | |
| 7 | 1 | 12/31/2005 | 6:00 PM | 300 | |

METHOD OF ENSURING DATE AND TIME ON A TEST METER IS ACCURATE

Studies have shown that people with diabetes who measure their blood glucose concentration about four times or more a day were found to more effectively maintain their glucose concentration in the euglycemic zone (about 70 mg/dL to about 180 mg/dL). After measuring their glucose concentration, a user would typically adjust their glucose concentration using an insulin injection or through other means such as diet or exercise. Reducing the number of wide swings in glucose concentration and maintaining a euglycemic state significantly reduced the occurrence of long term diabetes related complications such as blindness, kidney failure, retinopathy, and heart disease. Therefore, there is a trend for people with diabetes who desire to improve their overall health to measure their glucose concentration more frequently.

Typically, a person will measure their glucose episodically using a finger stick and a disposable test strip. Many people with diabetes will not perform more than four finger stick glucose measurements a day because of the inconvenience. In an effort to further improve the health of people with diabetes, continuous glucose monitors (CGM's) have been developed to conveniently measure glucose much more frequently than 4 times a day. CGM's have the ability to provide an immense number of glucose concentrations over an extended time period.

Software applications have been developed to process a large number of glucose concentrations into an easy to understand format. The trends within a large number of glucose concentrations may hold valuable insight for helping a person with diabetes more effectively manage their disease state. For example, OneTouch® Diabetes Management Software v2.3.1 allows a OneTouch® glucose meter to upload data to a computer for creating intelligent analytical reports that can be used by healthcare professionals to make quick and informed therapy decisions.

There is an effort to provide a hypoglycemic alarm based on trends in the glucose concentrations with time. Hypoglycemic events are very dangerous because they can result in a loss of consciousness and in some instances cause death. To properly interpret glucose trends with time, it is of paramount importance that the correct date and time be recorded with each glucose measurement. If a glucose measurement is recorded with an incorrect date and time value, then the glucose trends cannot be properly analyzed.

Accordingly, applicants heretofore provide for an invention that ameliorates the drawbacks of the known test meter. In one aspect, a method of operating a glucose test meter is provided. The method can be achieved by storing a plurality of glucose readings to a first memory of the test meter, each of the glucose readings having a time stamp and an order index, the time stamp comprising a date and a time when the glucose reading was performed, the order index indicating an order in which the plurality of glucose readings was saved to the first memory; determining whether successively saved glucose readings have time stamps in chronological order consistent with the order index; and indicating that the date and the time setting in the test meter is incorrect if there are successively saved glucose readings having time stamps inconsistent with the order index.

In yet another aspect, a method of operating a diabetes management system is provided. The method can be achieved by storing a plurality of glucose readings to a first memory of a test meter, each of the glucose readings having a time stamp and an order index, the time stamp comprising a date and a time when the glucose reading was performed, the order index indicating an order in which the plurality of glucose readings was saved to the first memory; transferring the plurality of glucose readings from the first memory of the test meter to a second memory of a computer; determining whether successively saved glucose readings have time stamps in chronological order consistent with the order index; and indicating that the date and the time setting in the test meter is incorrect if there are successively saved glucose readings having time stamps inconsistent with the order index.

In yet a further aspect, a glucose test meter is provided that includes a housing, test strip port, microprocessor and a display. The test strip port is disposed on the housing and configured to provide electrical signals representative of a glucose concentration from a blood sample on a test strip. The microprocessor is coupled to the test strip port and a memory so that a plurality of glucose readings from respective blood samples are stored in the memory with each glucose reading having a time stamp and an index of the order in which the glucose reading is stored. The display is controlled by the microprocessor so that a notification message is displayed when the plurality of glucose readings are inconsistent in chronological order with respect to the order index stored in the memory.

These and other embodiments, features and advantages will become apparent to those skilled in the art when taken with reference to the following more detailed description of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which.

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
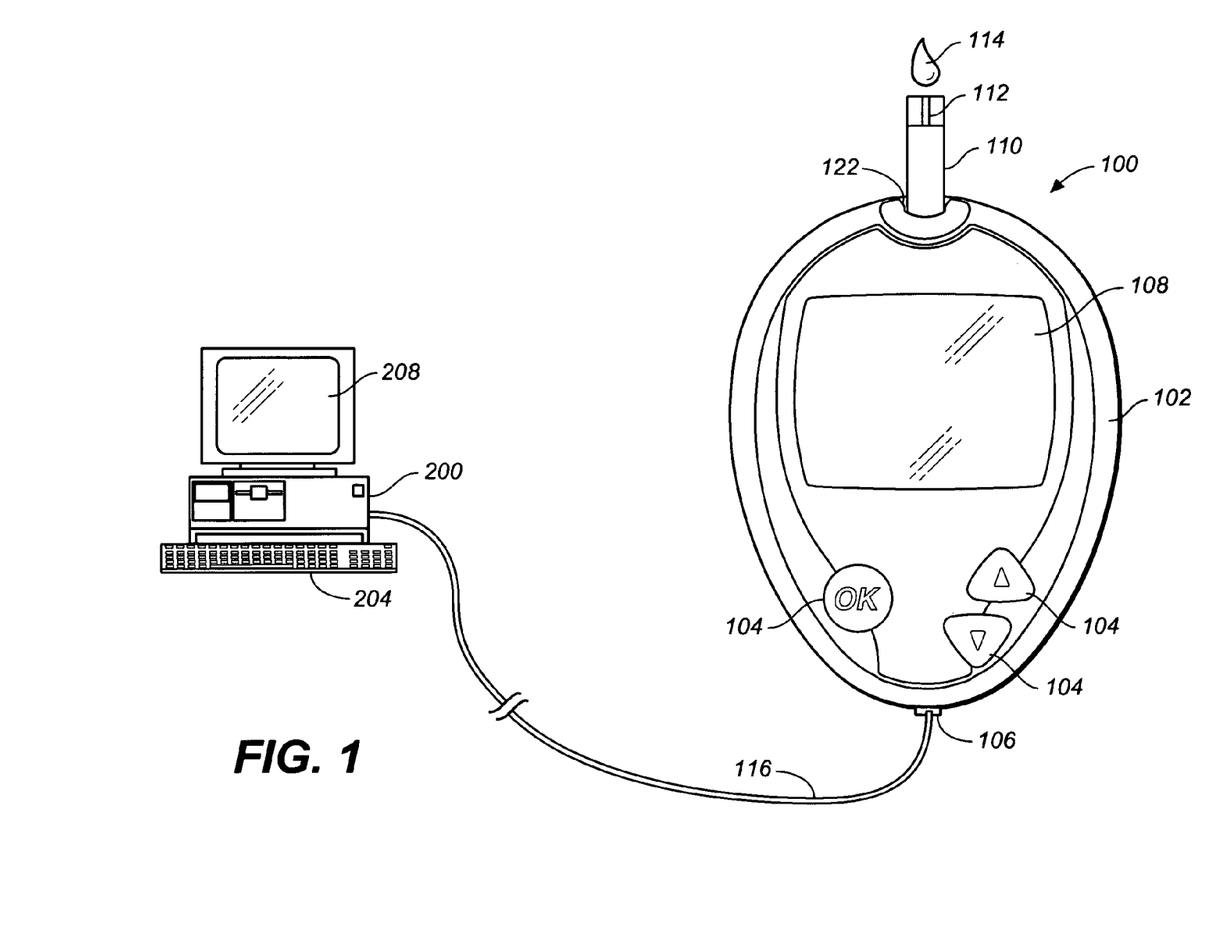
FIG. 1 illustrates a top plan view of a test meter that is connected to a test strip and also to a computer.
Figure 2:
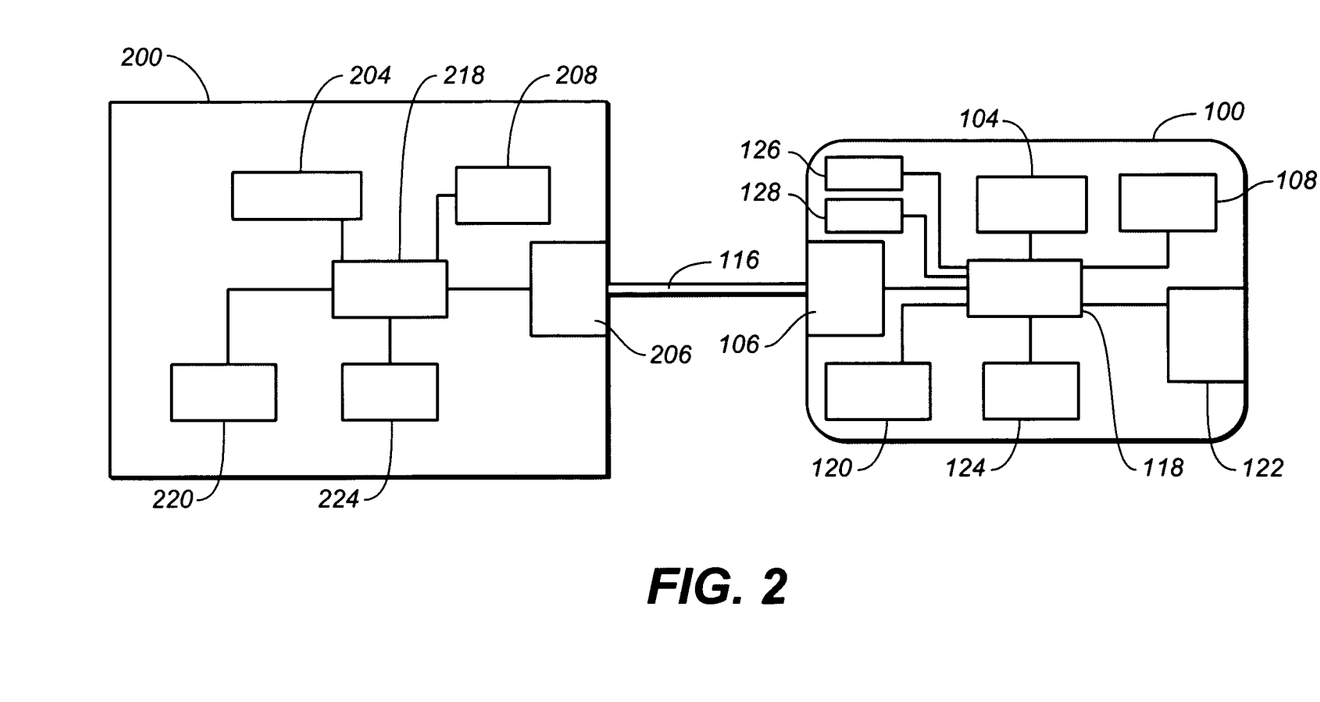
FIG. 2 illustrates a schematic of the functional components of the computer and of the test meter of FIG. 1.

FIG. 1 illustrates a test meter 100 suitable for connecting to a test strip 110 for analyzing a blood sample 114. Test meter 100 may also be connected to a computer 200, as illustrated in FIG. 1. Test meter 100 may include a housing 102, a plurality of user interface buttons 104, a first data port 106, a first display 108, and a strip port connector (SPC) 122, as illustrated in FIG. 1. Test meter 100 may further include a first microprocessor 118, a first memory 120, a first clock 124, electronic components for applying a test voltage 126, and electronic components for measuring a plurality of test current values 128, as illustrated in FIG. 2. First display 108 may show a glucose concentration and also may be used to show a user interface for prompting a user on how to perform a test. The plurality of user interface buttons 104 allow a user to operate test meter 100 by navigating through the user interface software.

Computer 200 may include a keyboard 204, a second data port 206, a second display 208, a second microprocessor 218, a second memory 220, and a second clock 224, as illustrated in FIGS. 1 and 2. Computer 200 may be connected to test meter 100 using a cable 116 connecting first data port 106 to second data port 206, as illustrated in FIG. 2. Other forms of a computer can also be utilized such as, for example, a lap-top, a personal computing assistant (e.g., a PALM) or a cellular phone.

Test strip 110 may be an electrochemical test strip for measuring glucose in blood. Blood sample 114 can be dosed into a sample receiving chamber 112 for performing an analysis. An example of a test strip suitable for use with the present invention may be an electrochemical test strip for glucose such as the commercially available OneTouch® Ultra® test strip (Milpitas, Calif.). Alternatively, a photochemical type test strip can also be utilized, such as, for example, OneTouch SureStep®.

Test meter 100 may be used to measure a plurality of glucose concentrations over a period of time. After each measurement, test meter 100 may output a glucose concentration value, and a date and time value that is shown on first display 108. The date and time value, which may also be referred to as a time stamp, may indicate when the measurement was performed. In addition, test meter 100 may save to first memory 120 the glucose concentration value and the time stamp.

Test meter 100 may have the ability to save a large number of glucose concentration values and the associated time stamps in first memory 120. In one embodiment, first memory 120 may be a form of flash memory configured to store up to about 20,000 entries. Previously tested glucose concentration values can be compiled into a report or log book showing a historical list of glucose concentrations and the associated time stamps for a pre-determined time period. A user can observe trends in the magnitude of glucose concentrations as a function of time. Further, a user may identify patterns such as an increased frequency of hypoglycemic or hyperglycemic events at particular time periods such as, for example, before or after a meal time. Yet further, a user may be able to predict the likelihood of a hypoglycemic or hyperglycemic even occurring in the future. In order for a user to take advantage of glucose trends as a function of time, it is very important that the time stamp be accurate. An inaccurate time stamp may cause a glucose measurement to be inaccurately recorded as being performed in the past or in the future. An error in a time stamp can potentially cause a significant error in analyzing a glucose trend.

Figure 3:
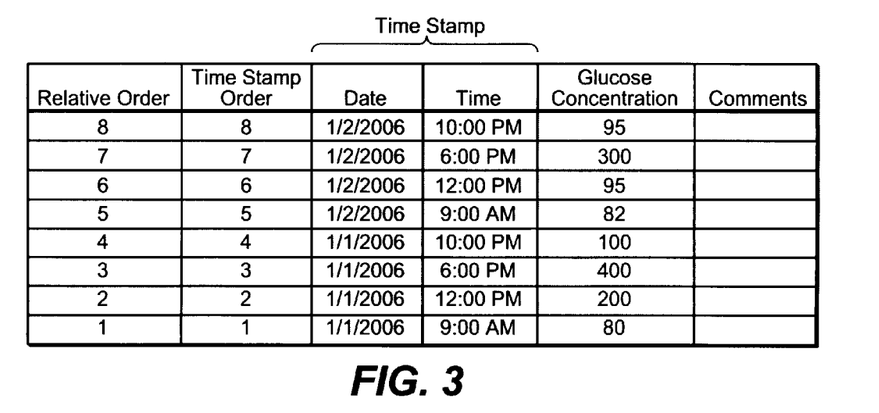
FIG. 3 illustrates an example of a data list report having a order index and time stamp order that are consistent.

FIG. 3 shows a plurality of glucose concentrations and time stamps illustrating an example of a data list report having a order index and a time stamp order that is consistent. A list organized by the time stamp order may be based on a chronological order ranging from the glucose reading having the oldest time stamp to the glucose reading having the most recent time stamp. A time stamp may be generated for each glucose measurement based on a reading from first clock 124. A order index may be based on the sequence in which a glucose concentration is saved to first memory 120 where the successive glucose concentrations are saved in a serial manner. The order index in which a glucose concentration is saved to first memory 120 is independent of the time stamp. A list organized by the order index may range from oldest glucose concentration saved to first memory 120 to the most recently measured glucose concentration saved to first memory 120. The order index and time stamp order should be the same because successively saved glucose measurements should be made in a chronologically increasing order.

A data list report may have an inconsistent order index and time stamp order if first clock 124 becomes inaccurate at some point during the collection of glucose readings for the data list report. There are several potential ways in which a test meter 100 may have the wrong date and time setting such as 1) a user did not set the date and time after purchasing test meter 100, 2) the battery in the test meter 100 discharged causing first clock 124 to lose the correct time and the user did not re-set first clock 124 after replacing the battery, 3) a user does not re-set first clock 124 after traveling to a different time zone, and 4) a user does not re-set first clock 124 after the occurrence of a daylight savings time. In many cases, the user may be completely unaware that their test meter 100 has an incorrect date and time setting.

Figure 4:
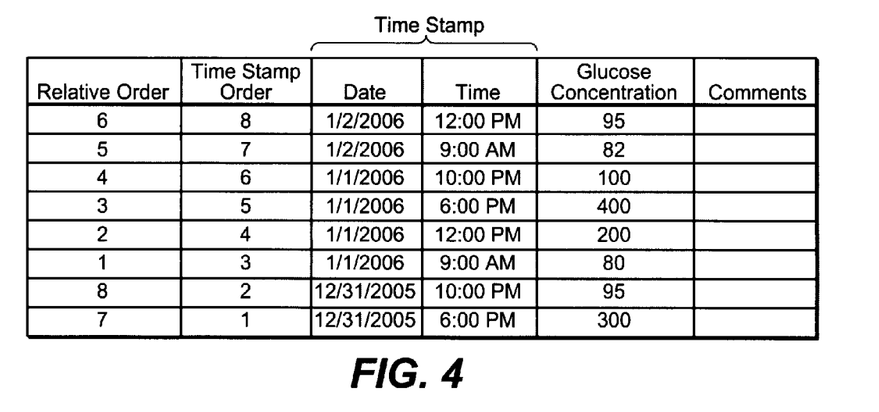
FIG. 4 illustrates an example of a data list report having a order index and time stamp order that are inconsistent.

FIG. 4 illustrates an example of a data list report having an order index and a time stamp order that are inconsistent. At some time after the sixth glucose measurement performed on 12:00 PM on Jan. 2, 2006, but before the seventh glucose measurement, first clock 124 either became re-set to a default value or was set incorrectly by the user. In FIG. 4, first clock 124 was set to an incorrect date and time setting after the sixth glucose measurement because the immediately subsequent measurements occurs in the past. The seventh and eighth measurements that are based on the order index occur before the first measurement based on the time stamp order, which is a non-sensical result.

Figure 5:
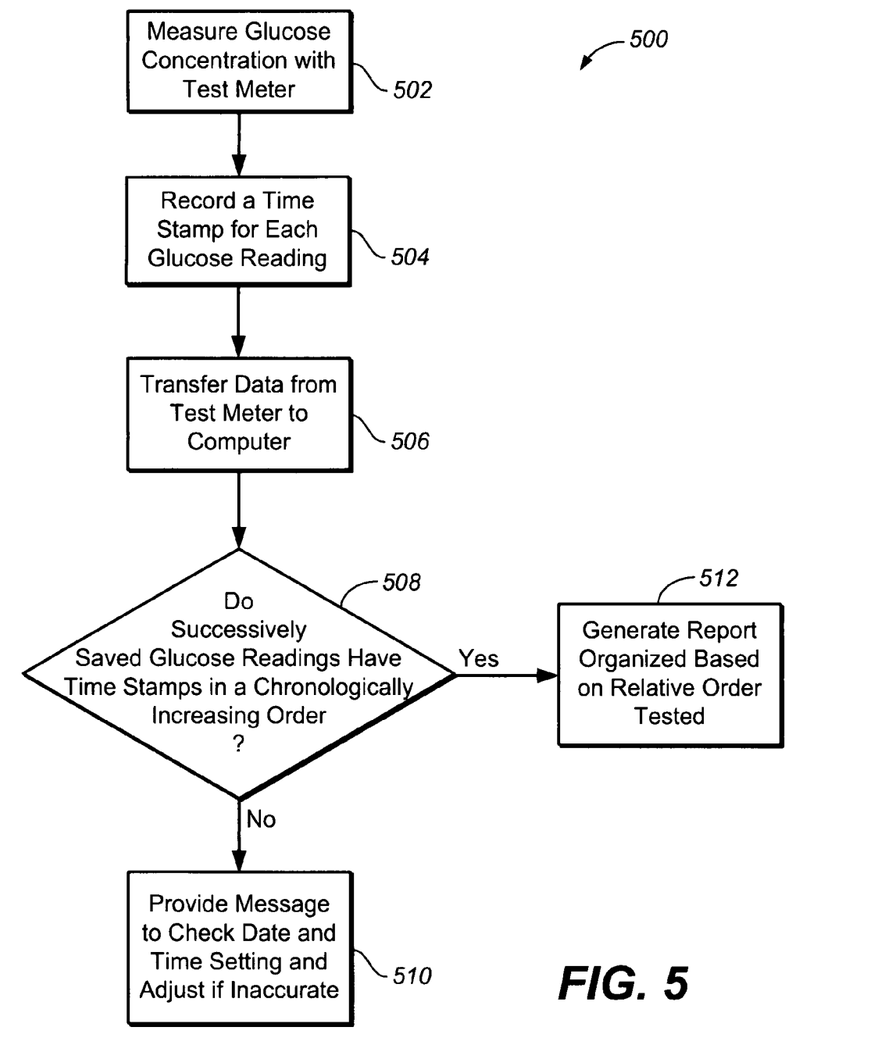
FIG. 5 illustrates a flow chart of a software application installed on a computer that is configured to detect an inconsistency in the time stamp order and the order index.

FIG. 5 illustrates a flow chart of a method 500 of ensuring a date setting and a time setting in a test meter 100 is accurate. Method 500 may be in the form of a software application installed on a second memory 220 on computer 200 that is configured to detect an inconsistency in the time stamp order and the order index when test meter 100 is connected to computer 200.

A user may perform a plurality of glucose measurements with test meter 100, as shown in step 502. The glucose reading, time stamp, and order index may all be recorded to first memory 120, as shown in step 504. The time stamp includes a date and a time indicating when the glucose measurement was performed based on first clock 124. The order index may indicate an order in which a glucose reading was saved to first memory 120 with respect to an immediately previous glucose reading and an immediately subsequent glucose reading. The glucose readings may be saved to first memory 120 in a serial manner such that the glucose readings are sequentially saved to first memory 120 independent of the time stamp value.

After performing a plurality of glucose measurements, test meter 100 may transfer data to computer 200, as shown in step 506. The data may be transferred by using cable 116 that electrically connects first data port 106 of test meter 100 to second data port 206 of computer 200. Alternatively, the glucose readings may be transferred by a wireless medium such as an infrared or RF transceivers. In one embodiment, the plurality of glucose measurements may be saved to second memory 220 on computer 200 in a serial manner based on the order index.

Figure 7:
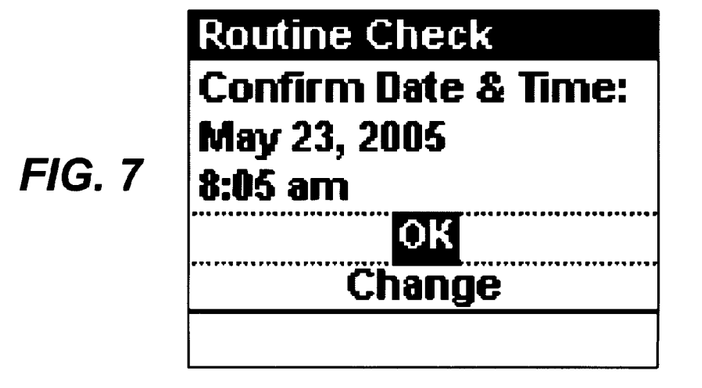
FIG. 7 illustrates a screen shot message that prompts a user to confirm a date and time setting on the test meter.

Second microprocessor 218 may determine whether successively saved glucose readings have time stamps consistent with a chronologically increasing order with respect to the order index, as shown in step 508. If there is one pair of successively saved glucose readings having time stamps inconsistent with a chronologically increasing order relative to the order index, then a message will be shown on second display 208 indicating that the date and time setting in test meter 100 is incorrect and should be confirmed for accuracy, as indicated in step 510. FIG. 7 shows an example of a message that prompts a user to confirm the date and time setting of test meter 100. If all of the successively saved glucose readings have time stamps consistent with a chronologically increasing order relative to the order index, then a report having a plurality of glucose concentrations and time stamps will be generated, as shown in step 512. FIG. 4 shows an example of a report having a plurality of glucose readings and time stamps that can be illustrated on second display 208.

First clock 124 may transmit a current date and time setting to computer 200. Second microprocessor 218 may calculate a difference between the current date and time setting of first clock 124 and second clock 224. If the difference is greater than a pre-determined threshold, then a warning message may be displayed on second display 208 indicating that first clock 124 is inaccurate. As an optional embodiment, the date and time setting of first clock 124 and second clock 224 may be simultaneously displayed on second display 208 for illustrating any discrepancy between the two date and time settings.

Within a dialog box containing a warning message, a user may be provided an option to automatically synchronize first clock 124 to second clock 224 every time test meter 100 is operatively connected to computer 200. Additionally, a user may also select the automatic time synchronization feature in the initial set up of the software application. After activating the automatic synchronization feature, first clock 124 will automatically synchronize to second clock 224 based on the assumption that second clock 224 will be more accurate. Second clock 224 may be more accurate if computer 200 periodically establishes communication to an external source having an accurate date and time setting. An example of an external time reference source may be a web site that uses an atomic clock for having a very accurate date and time setting, which can be transmitted to computer 200. Another example of an external time reference source may be a reference clock on a local area network that synchronizes periodically with computer 200 through a network connection. Yet another example can be an external time reference source that broadcasts time signals on a suitable FM wavelength.

Figure 6:
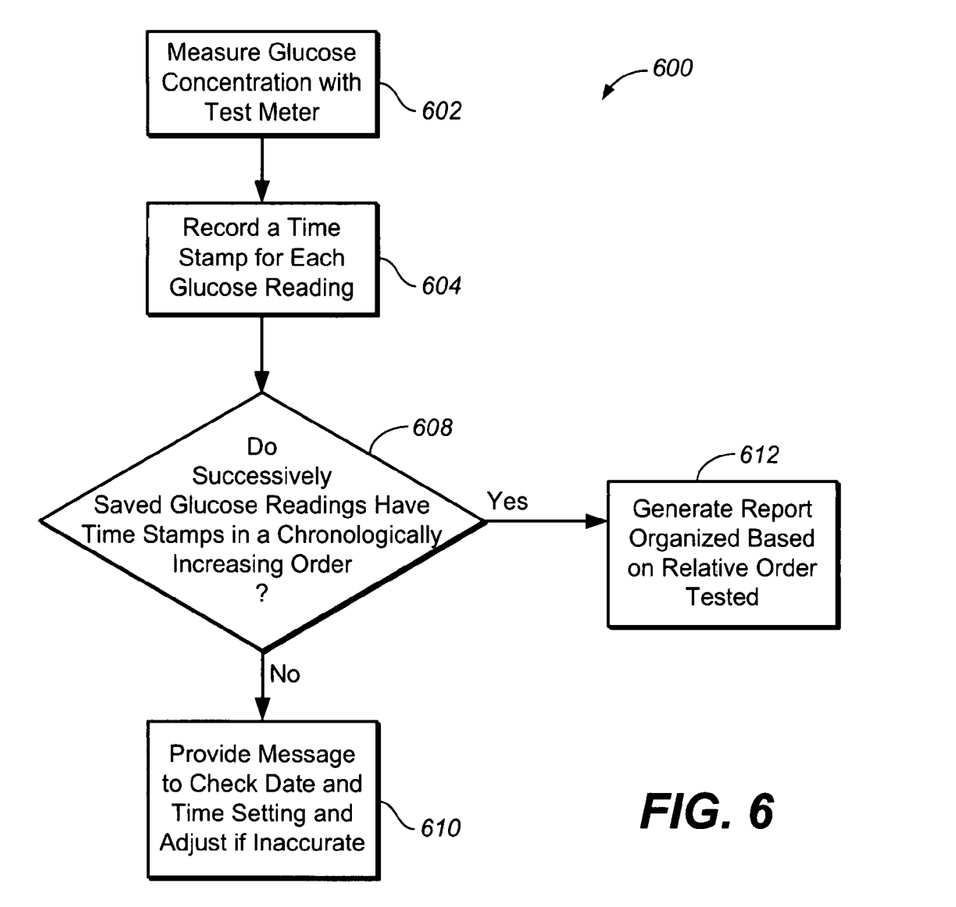
FIG. 6 illustrates a flow chart of a software application installed on the test meter that is configured to detect an inconsistency in the time stamp order and the order index.

FIG. 6 illustrates a flow chart of a method 600 of ensuring a date setting and a time setting in test meter 100 is accurate. In contrast to the method in FIG. 5, the method in FIG. 6 does not require computer 200. The method may be in the form of a firmware application installed on a first memory 120 that is configured to detect an inconsistency in the time stamp order and the order index.

A user may perform a plurality of glucose measurements with test meter 100, as shown in step 602. The glucose reading, time stamp, and order index may all be recorded to first memory 120, as shown in step 604. The time stamp includes a date and a time indicating when the glucose measurement was performed based on first clock 124. The order index may indicate an order in which a glucose reading was saved to first memory 120 with respect to an immediately previous glucose reading and an immediately subsequent glucose reading. The glucose readings may be saved to first memory 120 in a serial manner such that the glucose readings are sequentially saved to first memory 120 independent of the time stamp.

First microprocessor 118 may determine whether successively saved glucose readings have time stamps consistent with a chronologically increasing order, as shown in step 608. If there is one pair of successively saved glucose readings having time stamps inconsistent with a chronologically increasing order, then a message will be shown on first display 108 indicating that the date and time setting in test meter 100 is incorrect and should be confirmed for accuracy, as indicated in step 610. FIG. 7 shows an example of a message that prompts a user to confirm the date and time setting of test meter 100. The message may provide a user the option to enter the date and time setting setup for test meter 100 allowing the user to correct the date and time setting. If all of the successively saved glucose readings have time stamps consistent with a chronologically increasing order, then a report having a plurality of glucose concentrations and time stamps will be generated, as shown in step 612. FIG. 4 shows an example of a report having a plurality of glucose readings and time stamps that can be illustrated on first display 108.

In another embodiment, method 600 may further include the step of displaying the date and time on a splash screen when powering on test meter 100. The splash screen may be the opening animation shown on first display 108 when turning on test meter 100. The action of turning on test meter 100 causes the current date and time setting based on first clock 124 to be shown on first display 108 that causes the user to be immediately aware of the date and time setting. If the user notices that the date and time setting is inaccurate, then the user will prompted to change the date and time setting to be more accurate.

Figure 8:
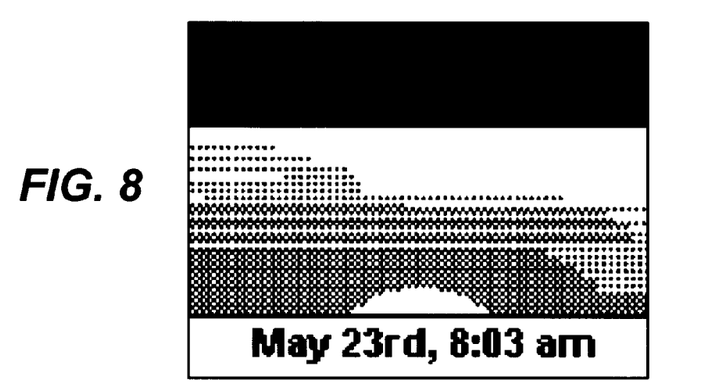
FIG. 8 illustrates a screen shot of a sunrise for that indicates to a user a general time period of the day.
Figure 9:
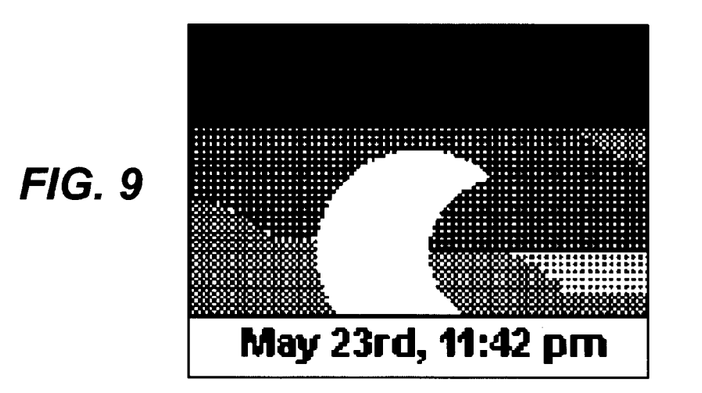
FIG. 9 illustrates a screen shot of a moon for that indicates to a user a general time period of the evening.

In yet another embodiment, method 600 may further include the step of displaying a sun icon or moon icon to indicate an approximate time when powering on test meter 100, as shown in FIGS. 8 and 9. The display of the sun icon or moon icon causes the user to be immediately aware of the approximate date and time setting. If the user notices that the date and time setting is inaccurate, then the user will prompted to change the date and time setting to be more accurate.

In a further embodiment, method 600 may further include the step of providing a user an option of inputting a flag indicating a pre or post-prandial glucose measurement and displaying the date and time on first display 108 when inputting the flag. The act of determining whether the glucose measurement was performed before or after eating a meal will prompt a user to be aware of the actual date and time of the measurement. Thus, a user will be more likely to notice whether the date and time setting is inaccurate. If the user notices that the date and time setting is inaccurate, then the user will prompted to change the date and time setting to be more accurate.

In an alternative embodiment, method 600 may further include a message on a display of test meter 100 to check the date and time setting in test meter 100 for accuracy at a pre-determined time interval. The pre-determined time interval may already be programmed into test meter 100. The act of prompting a user to periodically check the date and time setting will cause a user to user will be more likely to notice whether the date and time setting is inaccurate. Thus, if a user notices that the date and time setting is inaccurate, then the user will prompted to change the date and time setting to a more accurate value. The pre-determined time interval may range from about once a week to about once a month. Additionally, a pre-determined time interval may be on a day for switching ahead one hour or behind one hour for daylight savings time.

In a further alternative embodiment, method 600 may further include the step of calculating an average time period between successive glucose measurements over a pre-determined time interval. In addition, the time period between the most recent glucose measurement and the immediately previous glucose measurement may be calculated. If the time period between the two most recent glucose measurements is significantly greater than the historical average time period between successive glucose measurements, then a message may be shown on first display 108 to check the date and time setting for accuracy.

Alternatively, if the time period between the two most recent glucose measurements is significantly greater than a predetermined threshold, then a message may be show on first display to check the date and time setting for accuracy. For example, a predetermined threshold may be one month. Thus if a user does not perform successive tests within a one month period, test meter 100 will display a message to check the date and time setting for accuracy. If a user notices that the date and time setting is inaccurate, then the user will prompted to change the date and time setting to be more accurate.

It is believed that one advantage of the various embodiments is in that the methods for ensuring the date and time setting allow for greater accuracy with minimal complexity. Various embodiments described herein do not require complex components such as real time clocks using a dedicated battery source for reducing the chance of having an inaccurate date and time setting. Similarly, no super capacitors are needed to provide a supply voltage for maintaining the operation of first clock 124 when changing batteries in the test meter 100.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A method of operating a glucose test meter, the test meter including a housing, test strip port, microprocessor and a first display, in which the test strip port is disposed on the housing and configured to provide electrical signals representative of a glucose concentration from a blood sample on a test strip, and the microprocessor is coupled to the test strip port and a first memory, the method comprising:
   measuring with the microprocessor a plurality of blood glucose concentration readings from blood samples with the glucose test meter;
   storing with the microprocessor the plurality of glucose concentration readings to the first memory of the test meter, each of the glucose readings having a time stamp comprising a date and a time when the glucose concentration reading was performed,
   generating with the microprocessor an order index and a time stamp index and in which the order index is defined upon a sequence when each of the plurality of glucose concentration readings was saved to the first memory, and the time stamp index is defined by a chronological listing of the time stamp wherein the order index in which each glucose concentration reading is saved to the first memory is independent of the time stamp for each glucose concentration reading;
   determining with the microprocessor whether successively saved glucose concentration readings have time stamps in chronological order that are consistent with the order index; and
   indicating with the microprocessor that the date and the time setting in the glucose test meter is incorrect if there are successively saved glucose concentration readings having time stamps inconsistent with the order index.

2. The method of claim 1 further comprising sorting using the microprocessor the plurality of glucose concentration readings based on the order index before determining whether successively saved glucose concentration readings have time stamps in chronological order consistent with the order index.

3. The method of claim 1 further comprising providing a report having a plurality of glucose concentration readings and time stamps on a second display if all successively saved glucose concentration readings have time stamps consistent chronologically with the order index.

4. The method of claim 1 further comprising:
   calculating a difference between a date and a time from a first clock in the glucose test meter, and a date and a time from a second clock in a computer, and
   providing a warning message indicating the date and the time in the first clock is incorrect, if the difference is greater than a pre-determined threshold.

5. The method of claim 4 further comprising
   displaying the date and the time from the first clock in the glucose test meter on a second display; and
   displaying a date and a time from the second clock in the computer on the second display.

6. The method of claim 1 further comprising:
   establishing a communication of data between the glucose test meter and an external time reference source; and
   synchronizing a first clock in the glucose test meter to the external time reference source.

7. The method of claim 6, wherein the external time reference source is a web site having an accurate time setting.

8. The method of claim 6, wherein the external time reference source is an atomic clock.

9. The method of claim 6 wherein the external time reference source is a second clock in a computer further comprising automatically synchronizing the first clock of the glucose test meter to the second clock of the computer every time the glucose test meter is connected to the computer.

10. A method of operating a diabetes management system having a computer, a test meter and at least one test strip, the test meter including a housing, test strip port, microprocessor and a first display, the computer including a computer processor and a computer memory, the test strip port is disposed on the housing and configured to provide electrical signals representative of a glucose concentration from a blood sample on a test strip, and the microprocessor is coupled to the test strip port and a memory for the test meter, the method comprising:

measuring with the microprocessor of the test meter a plurality of glucose concentration readings with the test meter;

storing with the microprocessor the plurality of glucose concentration readings to the meter memory of the test meter in an order index serially based on the sequence in which the glucose concentration readings are saved to the meter memory, each of the glucose readings having a time stamp comprising a date and a time when the glucose concentration reading was performed, wherein the order index in which a glucose concentration reading is saved to the first memory is independent of the time stamp of the glucose concentration reading;

transferring with the microprocessor the plurality of glucose concentration readings from the first memory of the test meter to the computer memory of a computer;

determining with the computer processor whether successively saved glucose concentration readings have time stamps in chronological order which are consistent with the order index; and indicating with the microprocessor that a date and a time setting in the test meter is incorrect if there are successively saved glucose concentration readings having time stamps inconsistent with the order index.

11. The method of claim 10 further comprising the step of sorting the plurality of glucose concentration readings based on the order index before determining whether successively saved glucose concentration readings have time stamps consistent with a chronologically increasing order with respect to the order index.

12. The method of claim 10 further comprising providing a report having a plurality of glucose concentration readings and time stamps on the first display of the test meter if all successively saved glucose concentration readings have time stamps consistent with a chronologically increasing order with respect to the order index.

13. The method of claim 10 further comprising displaying the time and the date on a splash screen of the first display when powering on the test meter.

14. The method of claim 10 further comprising at least one icon to indicate an appropriate time.

15. The method of claim 10 further comprising continuously displaying the time and the date on the first display.

16. The method of claim 10 further comprising:

providing a user an option of inputting a flag indicating a pre or post-prandial glucose measurement; and displaying the time and the date on the first display of the test meter when inputting the flag.

17. The method of claim 10 further comprising providing a message on the first display of the test meter to check the date and the time setting in the test meter for accuracy at a pre-determined time interval programmed into the test meter.

18. The method of claim 17, wherein the pre-determined time interval is every week.

19. The method of claim 17, wherein the pre-determined time interval is every month.

20. The method of claim 10 further comprising providing a message on the first display to check the date and the time setting for accuracy on a day for switching to daylight savings time.

21. The method of claim 10 further comprising providing a message on the first display of the test meter to check the date and the time setting in the test meter for accuracy when a user performs a test at a time interval in which a user has an average historical testing frequency below a pre-determined threshold.

22. The method of claim 10 further comprising providing a message on the first display of the test meter to check the date and the time setting in the test meter for accuracy when an amount of time has passed between two successive glucose measurements and the amount of time is greater than a pre-determined threshold.

* * * * *